(12) United States Patent
Moberg et al.

(10) Patent No.: US 7,666,217 B2
(45) Date of Patent: Feb. 23, 2010

(54) IMPLANTABLE MEDICAL ENDOPROSTHESIS DELIVERY SYSTEMS AND RELATED COMPONENTS

(75) Inventors: John R. Moberg, Elk River, MN (US); Gary Pederson, Maple Grove, MN (US); Richard C. Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 323 days.

(21) Appl. No.: 10/977,098

(22) Filed: Oct. 29, 2004

(65) Prior Publication Data

US 2006/0095110 A1 May 4, 2006

(51) Int. Cl.
*A61F 2/06* (2006.01)

(52) U.S. Cl. .................................................. 623/1.11

(58) Field of Classification Search ............... 623/1.11, 623/1.12; 606/159, 194, 108
See application file for complete search history.

(56) References Cited

U.S. PATENT DOCUMENTS

| | | | |
|---|---|---|---|
| 4,530,855 A | 7/1985 | Youngkeit | |
| 4,554,929 A * | 11/1985 | Samson et al. | 600/585 |
| 4,840,623 A | 6/1989 | Quackenbush | |
| 4,861,621 A | 8/1989 | Kanzaki | |
| 4,862,922 A | 9/1989 | Kite, III | |
| 5,107,852 A * | 4/1992 | Davidson et al. | 600/585 |
| 5,137,513 A * | 8/1992 | McInnes et al. | 604/103.05 |
| 5,314,438 A * | 5/1994 | Shturman | 606/159 |
| 5,342,300 A | 8/1994 | Stefanadis et al. | |
| 5,531,719 A | 7/1996 | Takahashi | |
| 5,534,007 A * | 7/1996 | St. Germain et al. | 623/1.11 |
| 5,593,394 A | 1/1997 | Kanesaka et al. | |
| 5,607,404 A | 3/1997 | Khairkhahan | |
| 5,607,531 A | 3/1997 | Needham et al. | |
| 5,614,139 A | 3/1997 | Cutolo et al. | |
| 5,643,278 A * | 7/1997 | Wijay | 623/1.11 |
| 5,662,675 A | 9/1997 | Polanskyj Stockert et al. | |
| 5,681,280 A | 10/1997 | Rusk et al. | |
| 5,681,296 A | 10/1997 | Ishida | |
| 5,690,643 A | 11/1997 | Wijay | |
| 5,788,707 A * | 8/1998 | Del Toro et al. | 623/1.11 |
| 5,882,347 A | 3/1999 | Mouris-Laan et al. | |
| 5,968,068 A | 10/1999 | Dehdashtian et al. | |
| 6,019,778 A | 2/2000 | Wilson et al. | |
| 6,045,734 A | 4/2000 | Luther et al. | |
| 6,096,045 A | 8/2000 | Del Toro et al. | |

(Continued)

FOREIGN PATENT DOCUMENTS

EP 1385450 3/2007

(Continued)

OTHER PUBLICATIONS

Schetsky, L. McDonald, "Shape Memory Alloys", Encyclopedia of Chemical Technology (3rd ed.), John Wiley & Sons, 1982, vol. 20, pp. 726-736.

(Continued)

*Primary Examiner*—Todd E Manahan
*Assistant Examiner*—Lindsey Bachman
(74) *Attorney, Agent, or Firm*—Crompton, Seager & Tufte, LLC (57) ABSTRACT

Implantable medical endoprosthesis delivery systems and related components, as well as related methods are disclosed.

22 Claims, 7 Drawing Sheets

U.S. PATENT DOCUMENTS

| | | | |
|---|---|---|---|
| 6,203,550 B1 | 3/2001 | Olson | |
| 6,302,893 B1 | 10/2001 | Limon et al. | |
| 6,342,066 B1 | 1/2002 | Toro et al. | |
| 6,368,344 B1 | 4/2002 | Fitz | |
| 6,607,551 B1 | 8/2003 | Sullivan et al. | |
| 6,663,660 B2 * | 12/2003 | Dusbabek et al. | 623/1.11 |
| 6,699,274 B2 | 3/2004 | Stinson | |
| 6,733,519 B2 | 5/2004 | Lashinski et al. | |
| 6,743,219 B1 | 6/2004 | Dwyer et al. | |
| 6,773,446 B1 | 8/2004 | Dwyer et al. | |
| 6,786,918 B1 | 9/2004 | Krivoruchko et al. | |
| 6,833,003 B2 * | 12/2004 | Jones et al. | 623/1.11 |
| 6,849,062 B2 | 2/2005 | Kantor | |
| 6,860,898 B2 * | 3/2005 | Stack et al. | 623/1.11 |
| 6,923,788 B2 | 8/2005 | Kantor | |
| 2002/0065475 A1 * | 5/2002 | Meguro et al. | 600/585 |
| 2002/0095203 A1 | 7/2002 | Thompson et al. | |
| 2003/0109886 A1 | 6/2003 | Keegan et al. | |
| 2004/0002727 A1 | 1/2004 | Hwang et al. | |
| 2004/0002728 A1 | 1/2004 | Speck et al. | |
| 2004/0049231 A1 | 3/2004 | Hafer | |
| 2004/0078071 A1 * | 4/2004 | Escamilla et al. | 623/1.11 |
| 2004/0097959 A1 | 5/2004 | Thompson | |
| 2004/0220585 A1 * | 11/2004 | Nikolchev | 606/108 |
| 2005/0065474 A1 | 3/2005 | Larson et al. | |

FOREIGN PATENT DOCUMENTS

| | | |
|---|---|---|
| WO | WO 02/056953 | 7/2002 |
| WO | WO 2004/096091 | 11/2004 |

OTHER PUBLICATIONS

PCT Search Report, International Application No. PCT/US2005/038975, mailed Jul. 5, 2006.

Invitation to Pay Additional Fees; PCT/US2005/038975; mailed Mar. 7, 2006.

* cited by examiner

IMPLANTABLE MEDICAL ENDOPROSTHESIS DELIVERY SYSTEMS AND RELATED COMPONENTS

TECHNICAL FIELD

This invention relates to implantable medical endoprosthesis delivery systems and related components, as well as related methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer member surrounding an inner member with a stent positioned therebetween. Generally, the operator of the system positions the distal portion within the lumen at a desired location (e.g., so that the stent is adjacent an occlusion). The operator can then retract the outer member to allow the stent to engage the occlusion/lumen wall. Thereafter, the operator removes the distal portion of the system from the lumen.

SUMMARY

In general, the invention relates to implantable medical endoprosthesis delivery systems and components, as well as related methods. The systems can be used, for example, to deliver an implantable medical endoprosthesis (e.g., a stent) at a desired location within a lumen of a subject (e.g., an artery of a human).

The implantable medical endoprosthesis delivery systems generally include an inner member having a tube that is surrounded by a coil and/or a spacer.

In embodiments in which a coil surrounds the tube, the coil typically includes one or more portions that are spaced outwardly from the tube, and one or more other portions that are supported by (e.g., in contact with) the tube. In some embodiments, the coil includes inner and outer portions that are formed of the same or different materials. For example, the inner portion of the coil can be a wire (e.g., a wire formed of a metal or alloy), and the outer portion of the coil can be a polymer (e.g., a thermoplastic) coated on the wire. In certain embodiments, the tube is surrounded by multiple coils.

In embodiments in which a spacer surrounds the tube, the spacer typically has at least two orifices that extend longitudinally therethrough. The tube is disposed in one of the orifices, and, when present in an implantable medical endoprosthesis delivery system, at least one of the orifices of the spacer in which the tube is not disposed allow for fluid flow between the tube and the outer member that at least partially surrounds the tube. In some embodiments, the tube is surrounded by multiple spacers.

In certain embodiments, an inner member can include a tube that is surrounded by one or more coils and one or more spacers.

The inner members can be sufficiently flexible for use in implantable medical endoprosthesis delivery systems, while also having a reduced surface area in contact with the outer member. This can, for example, reduce the force used to retract the outer member during deployment of the implantable medical endoprosthesis (e.g., stent), which can result in little or no compression or buckling of the inner member tube. This can enhance the accuracy of placement of the medical endoprosthesis (e.g., stent) during deployment. Optionally, the deployment force can be further reduced by forming the tube, outer member, coil and/or spacer of a material having a relatively low coefficient of friction.

Alternatively or additionally, the systems can provide good fluid flow between the inner and outer members. For example, the systems can provide good flow of dye (e.g., fluoroscopic dye) between the tube and the outer member, which can aid in delivery of the systems to a desired site within a subject (e.g., a human) and/or aid in the deployment of the implantable medical endoprosthesis (e.g., stent) at a desired site (e.g., an artery of a human).

Other features and advantages of the invention will be apparent from the description, drawings and claims.

DESCRIPTION OF DRAWINGS

Like reference symbols in the various drawings indicate like elements.

DETAILED DESCRIPTION

Figure 1:
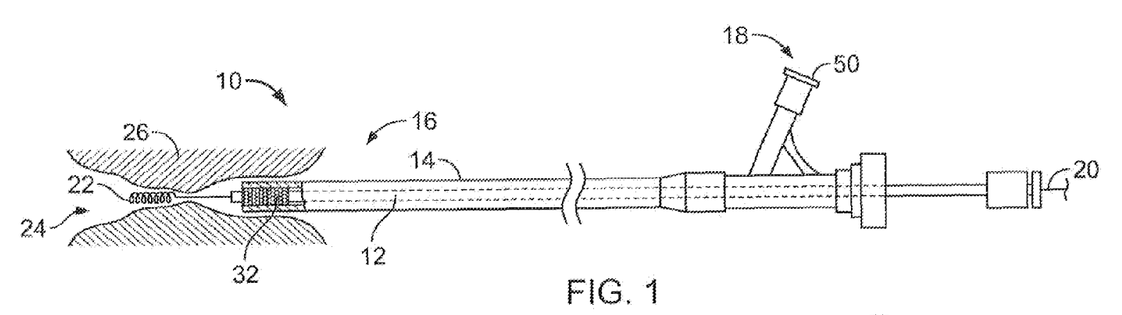
FIGS. 1-3 are side views of an embodiment of an endoprosthesis delivery system during use.
Figure 2:
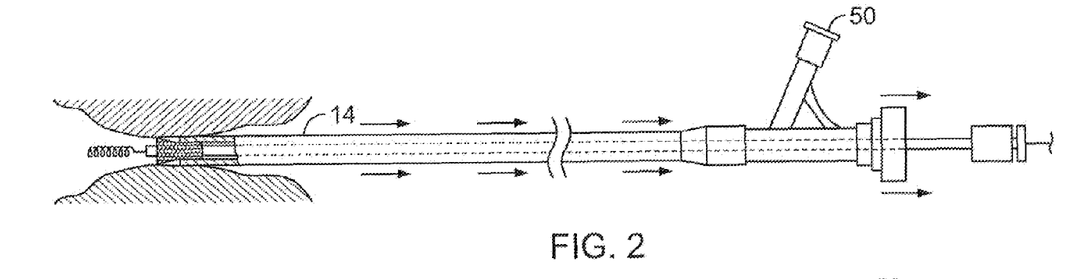
Figure 3:
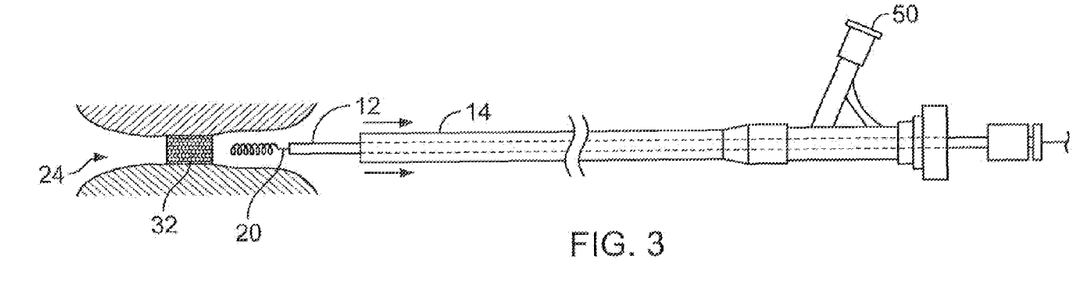

FIGS. 1-3 show an implantable medical endoprosthesis delivery system 10 that includes an inner member 12, an outer member 14 surrounding inner member 12, and a stent 32 positioned between inner member 12 and outer member 14. The delivery system 10 includes a distal end 16 dimensioned for insertion into a body lumen (e.g., an artery of a human) and a proximal end 18 that resides outside the body of a subject, and that contains at least one port 50 and lumens for manipulation by a physician. A guide wire 20 with a blunted end 22 is inserted into a body lumen 24 by, for example, making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, inner member 12, stent 32 and outer member 14 are placed over the proximal end of guide wire 20. Inner member 12, stent 32 and outer member 14 are moved distally over guide wire 20 and positioned within lumen 24 so that stent 32 is adjacent constricted site 26 of lumen 24. Outer member 14 is moved proximally, allowing stent 32 to expand and engage constricted site 26. Outer member 14, inner member 12 and guide wire 20 are removed from body lumen 24, leaving stent 32 engaged with constricted site 26.

Figure 4:
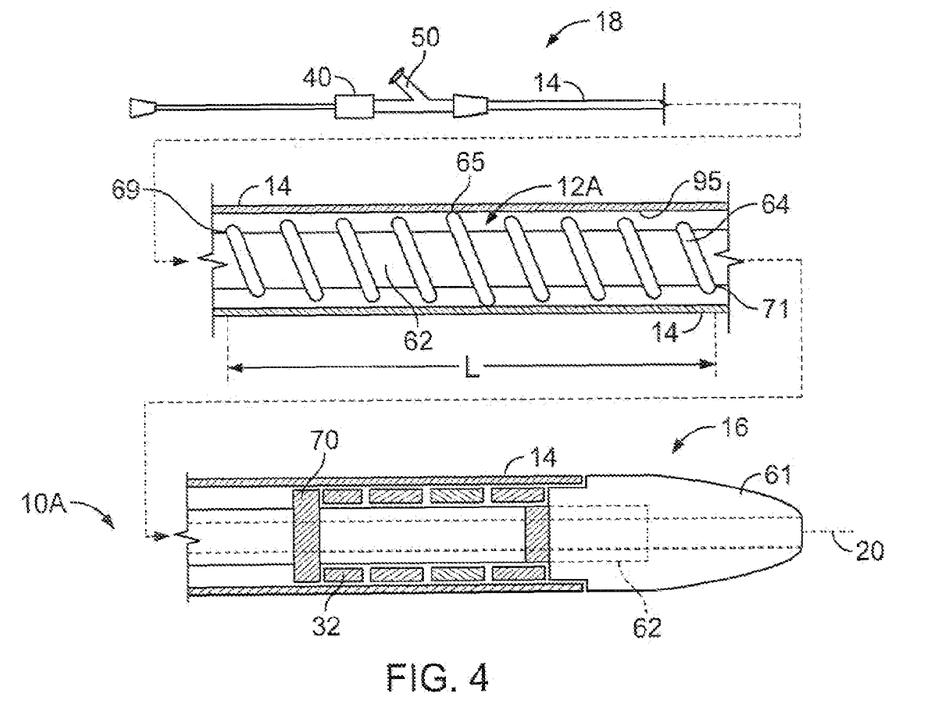
FIG. 4 is an exploded, mixed view of an embodiment of an endoprosthesis delivery system.
Figure 5:
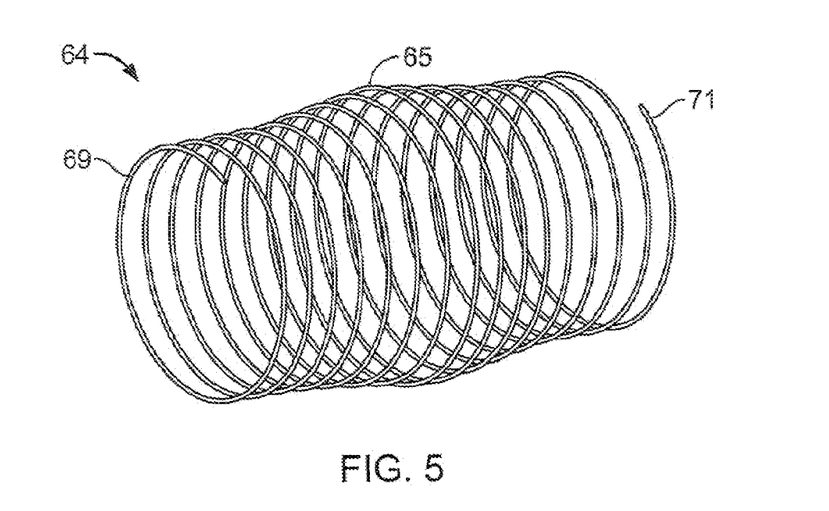
FIG. 5 is a perspective view of an embodiment of a coil.

FIG. 4 shows an implantable medical endoprosthesis system 10A in which an inner member 12A includes a tube 62 surrounded by a coil 64. As shown in FIGS. 4 and 5, coil 64 includes ends 69 and 71 that contact tube 62, and a portion 65 that is spaced outwardly from tube 62 so that coil 64 separates tube 62 from outer member 14 and also reduces the surface area of outer member 14 that contacts inner member 12A. With this arrangement, coil 64 can allow fluid to flow between tube 62 and outer member 14. For example, a fluoroscopic dye fluid can flow between tube 62 and outer member 14 to assist in delivering system 10A in a subject and/or to assist in deploying stent 32 at a desired site. Coil 64 also reduces the surface area of inner member 12A in contact with outer member 14, which can reduce the force used to retract outer member 14 during deployment of stent 32. This can reduce (e.g., eliminate) compression or buckling of tube 62 as outer member 14 is retracted, which can enhance the accuracy of placement of stent 32 in a desired location.

Figure 6A:
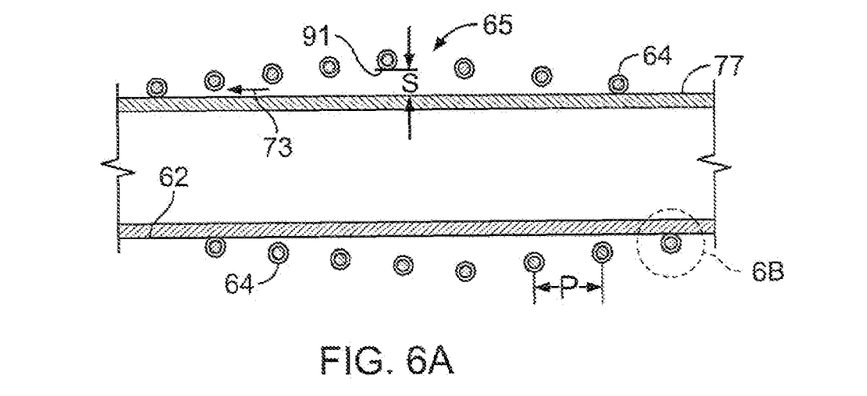
FIG. 6A is a longitudinal cross-sectional view of a portion of the inner member shown in FIG. 4.
Figure 6B:
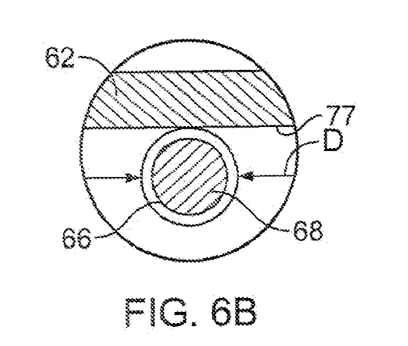
FIG. 6B is an enlarged view of area 6B shown in FIG. 6A.
Figure 7:
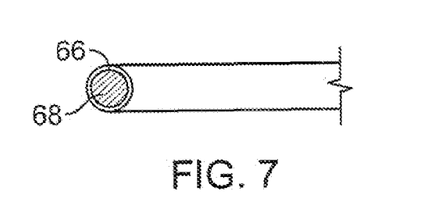
FIG. 7 is a perspective view of a portion of an embodiment of a coil, illustrating inner and outer portions.

As shown in FIGS. 6A, 6B and 7, coil 64 includes an inner portion 68 that is surrounded by an outer portion 66. Inner portion 68 can be, for example, a wire formed of a material having the appropriate flexibility and strength. Examples of materials include metals, alloys and polymeric materials. Examples of metals include platinum, gold and stainless steel. Examples of alloys include gold-containing alloys, platinum-containing alloys, stainless steel and shape memory alloys. Examples of shape memory alloys include nitinol, silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc (Cu—Zn), copper-zinc-aluminum (Cu—Zn—Al), copper-zinc-tin (Cu—Zn—Sn), copper-zinc-xenon (Cu—Zn—Xe), iron beryllium ($Fe_3Be$), iron platinum ($Fe_3Pt$), indium-thallium (In—Tl), iron-manganese (Fe—Mn), nickel-titanium-vanadium (Ni—Ti—V), iron-nickel-titanium-cobalt (Fe—Ni—Ti—Co) and copper-tin (cu—Sn), for yet additional shape memory alloys, see, for example, Schetsky, L. McDonald, "Shape Memory Alloys", *Encyclopedia of Chemical Technology* (3rd ed.), John Wiley & Sons, 1982, vol. 20 pp. 726-736. Examples of polymeric materials include polyamides (e.g., nylons), thermoplastic polyester elastomers (e.g., Hytrel®), copolyester elastomers (e.g., Arnitel® copolyester elastomers), polyether-block co-polyamide polymers (e.g., PEBAX®) and high-density polyethylene (HDPEs).

Outer portion 66 can be, for example, a polymeric material, such as a plastic (e.g., a thermoplastic) or a thermoset. Examples of polymeric materials include polyamides (e.g., nylons), polyurethanes, styrenic block copolymers, nylons, thermoplastic polyester elastomers (e.g., Hytrel®), copolyester elastomers (e.g., Arnitel® copolyester elastomers), polyether-block co-polyamide polymers (e.g., PEBAX®), fluoropolymers (e.g., PTFE, FEP) and HDPEs. In some embodiments, outer portion 66 is integral with an outer surface 77 of tube 62 at ends 69 and/or 71 of coil 64. This can, for example, assist in maintaining the position of coil 64 constant with respect to tube 62. In certain embodiments, portion 66 of tube 64 includes a coefficient of friction-reducing additive (e.g., a fluoropolymer, a silicone, an ultrahigh molecular weight polyethylene, an oil, or blends thereof) to assist in the movement of outer member 14 with respect to inner member 12A and stent 32. Examples of fluoropolymers include PTFE and FEP.

In certain embodiments, the longitudinal length, L, (FIG. 4) of coil 64 is from about 0.1 inch to about one inch (e.g. from about 0.25 inch to about 0.75 inch). For example, the longitudinal length of each coil can be about 0.25 inch, about 0.5 inch or about 0.75 inch.

In general, coil 64 can have a pitch between adjacent windings of, for example, from at least 0.005 inch (e.g., at least 0.01 inch, at least about 0.05 inch) and/or at most about 0.1 inch (e.g., at most about 0.075 inch, at most about 0.06 inch). In certain embodiments, the pitch of coil 64 is from 0.005 inch to about 0.1 (e.g., from 0.01 inch to about 0.06 inch, from about 0.05 inch to about 0.06 inch).

In some embodiments, coil 64 is circular in cross-section with a diameter, D, (FIG. 6B) of at least 0.002 inch (e.g., at least 0.004 inch) and/or at most 0.01 (e.g., at most 0.005 inch). For example, in certain embodiments, the diameter, D, of coil 64 can be from 0.002 inch to about 0.01 inch (e.g., from 0.004 inch to 0.006 inch, 0.005 inch).

The spacing, S, between an outer surface 77 of tube 62 and an inner surface 91 of coil 64 at portion 65 can generally be selected as desired. In some embodiments, the spacing, S, is from 0.005 inch to 0.1 inch (e.g., from 0.01 inch to 0.75 inch). For example, the spacing, S, can be 0.025 inch or 0.075 inch.

Stent 32 is typically formed of a shape memory alloy. Examples of shape memory alloys include those discussed above. Other stent materials are known in the art.

In general, tube 62 is made of a polymeric material. Examples of polymeric materials include polyether-block copolyamide polymers (e.g., PEBAX®), copolyester elastomers (e.g., Amitel® copolyester elastomers), thermoplastic polyester elastomers (e.g., Hytrel®), thermoplastic polyurethane elastomers (e.g., Pellethane™), polyeolefins (e.g., Marlex® polyethylene, Marlex® polypropylene), HDPEs, low-density polyethylenes (LDPEs), polyamides (e.g., nylons, Vestamid®), and combinations of these materials. In certain embodiments, tube 62 includes a coefficient of friction-reducing additive (e.g., a fluoropolymer, a silicone, an ultrahigh molecular weight polyethylene, an oil, or blends thereof) to assist in the movement of outer member 14 with respect to inner member 12A and stent 32. Examples of fluoropolymers include PTFE and FEP.

Typically, outer member 14 is made of a polymeric material. Examples of polymeric materials include those noted above with respect to tube 62. In some embodiments, outer member 14 includes a coefficient of friction-reducing additive (e.g., a fluoropolymer, a silicone, an ultrahigh molecular weight polyethylene, an oil, or blends thereof) to assist in the movement of outer member 14 with respect to inner member 12A and stent 32. Examples of fluoropolymers include PTFE and FEP.

As shown in FIG. 4, system 10A can further include a bumper 70 that is integral with tube 62, and a tip 61 that is integral with tube 62. Bumper 70 can reduce the possibility of stent 32 moving proximally as outer member 14 is retracted proximally, and tip 61 can assist in positioning of system 10A within body lumen 26 (e.g., as system 10A is moved distally over guide wire 20 within body lumen 24). In some embodiments, bumper 70 is formed of a polymeric material, such as a polyether-block co-polyamide polymer (e.g., PEBAX®) or a thermoplastic polyurethane elastomer (e.g., Pellethane™). In certain embodiments, bumper 70 is made of a metal or an alloy, such as, for example, stainless steel, Nitinol and/or platinum. Tip 61 is typically formed of a relatively soft polymeric material.

Figure 8:
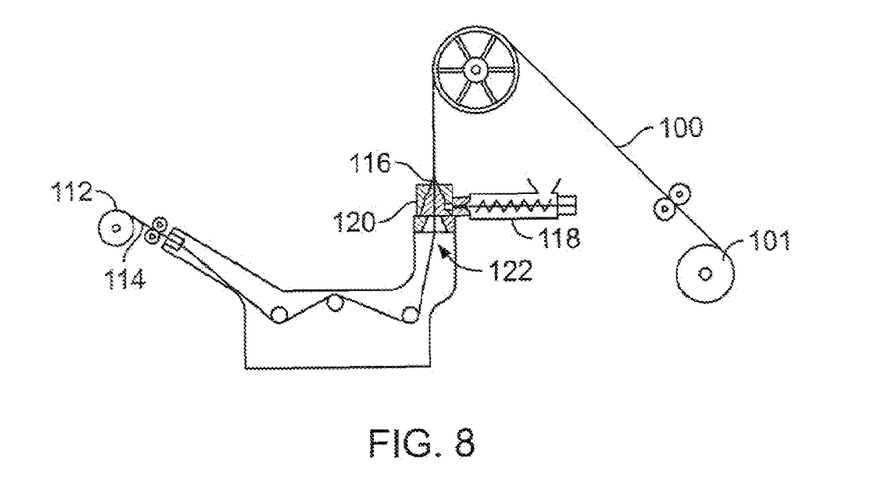
FIG. 8 is a schematic view illustrating a portion of an embodiment of a process for coating a wire.

Although shown as including a single coil, in some embodiments inner member 12A can include multiple longitudinally spaced apart coils (e.g., two longitudinally spaced apart coils, three longitudinally spaced apart coils, four longitudinally spaced apart coils, five longitudinally spaced apart coils, six longitudinally spaced apart coils, seven longitudinally spaced apart coils, eight longitudinally spaced apart coils, nine longitudinally spaced apart coils, 10A longitudinally spaced apart coils) that surround tube 62. Referring to FIG. 8, for example, inner member 12A includes multiple longitudinally spaced apart coils 64A, 64B that surround tube 62. Typically, coils 64A and 64B have a design as described above with respect to coil 64. In some embodiments, the longitudinal spacing between nearest neighboring separate coils is from about 0.1 inch to about one inch (e.g., from about 0.25 inch to about 0.75 inch). For example, the longitudinal spacing between nearest neighboring separate coils can be about 0.25 inch, about 0.5 inch, or about 0.75 inch. In certain embodiments, the longitudinal length of each coils is from about 0.1 inch to about one inch (e.g., from about 0.25 inch to about 0.75 inch), for example, the longitudinal length of each coil can be about 0.25 inch, about 0.5 inch or about 0.75 inch.

In general, inner member 12A including tube 62 and coil 64 can be prepared as desired. In some embodiments, inner member 12A can be prepared as follows.

A wire having a transverse cross-section similar to that of coil 64 is prepared. FIG. 8 illustrates an embodiment of a pultrusion process for a making a wire 100. A spool 112 of a metallic filament (e.g., stainless steel wire) 114 is pulled through a fluid polymeric material (e.g., molten thermoplastic) 116 that is pumped onto filament 114 by extruder 118 as filament 114 passes through a die 120 with an aperture 122. After exiting die 120, wire 100 is collected on a spool 101. Pultrusion processes are disclosed, for example, in U.S. Pat. Nos. 4,530,855, 4,861,621, 4,862,922, 5,607,531 and 5,614,139. Equipment for performing pultrusion processes is commercially available from, for example, Entec Composite Machines, Salt Lake City, Utah (USA) and Pultrex, Essex (UK).

Figure 9:
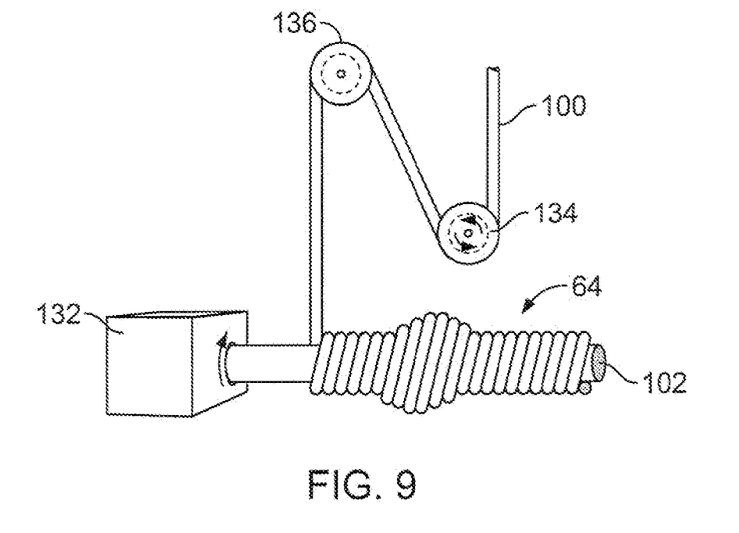
FIG. 9 is a schematic view, illustrating a portion of an embodiment of a process for forming a coil.
Figure 10:
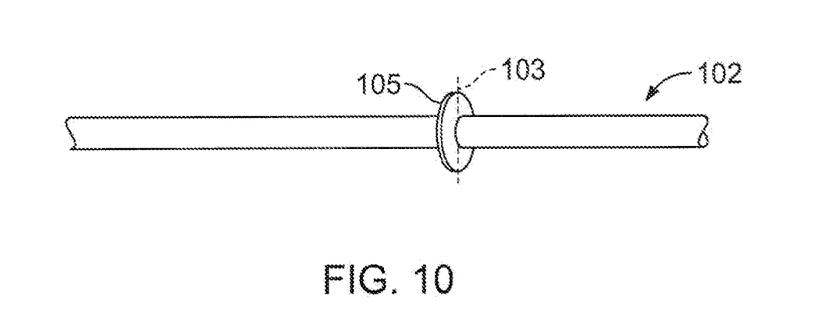
FIG. 10 is a perspective view of a mandrel.

Wire 100 is then formed into a coil. FIG. 9 shows an embodiment of a process for forming wire 100 into a coil by winding wire 100 around a mandrel 102 as mandrel 102 is rotated by a motor 132. Wire 100 is supplied to mandrel 102 via a main tension pulley 134 and a cantilevered pulley 136. Generally, mandrel 102 is several inches (e.g., about two inches) longer than the desired coil length. Mandrel 102 can include a portion having a relatively large outer diameter, which corresponds to portion 65 of coil 64. Filament winding processes are disclosed, for example, in U.S. Pat. Nos. 5,335,167 and 5,601,599. Filament winding equipment is commercially available from, for example, Pultrex, Essex (UK). Wound wire 100 is removed from mandrel 102 to provide coil 64 (FIG. 5). FIG. 10 shows an embodiment of mandrel 102 that is split along a line 103 that bisects feature 105. Feature 105 forms portion 65 of coil 64. This split design can aid in removal of mandrel 102 from interior portions of coil 64. In some embodiments, the coil can be prepared by winding the wire (e.g., a NiTi wire) on a form mandrel and heat setting it to create a superelastic NiTi coil.

Figure 11:
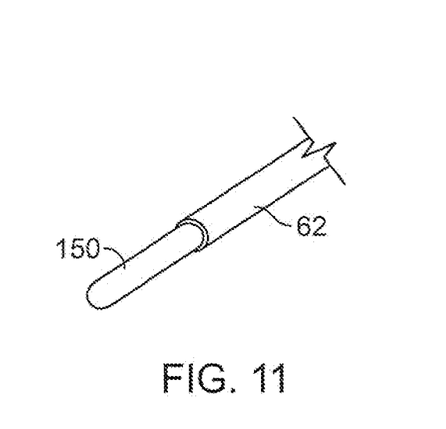
FIG. 11 is a side view of an embodiment of a portion of a tube disposed around a support.

Referring to FIG. 11, tube 62 is placed around a support member 150, and then coil 64 is placed around tube 62. Coil 64 is made integral with tube 62 to provide inner member 12A (see discussion above). Support member 150 reduces the possibility of tube 62 being undesirably deformed during subsequent processing. After being positioned around tube 62, coil 64 can be made integral with tube 62 by exposure to energy (e.g., heat, UV, IR). In some embodiments, outer material 66 of coil 64 is a thermoplastic material, and coil 64 can be made integral with tube 62 by heating outer material 66 with a heat gun so that outer material 66 is welded to tube 62.

Figure 12:
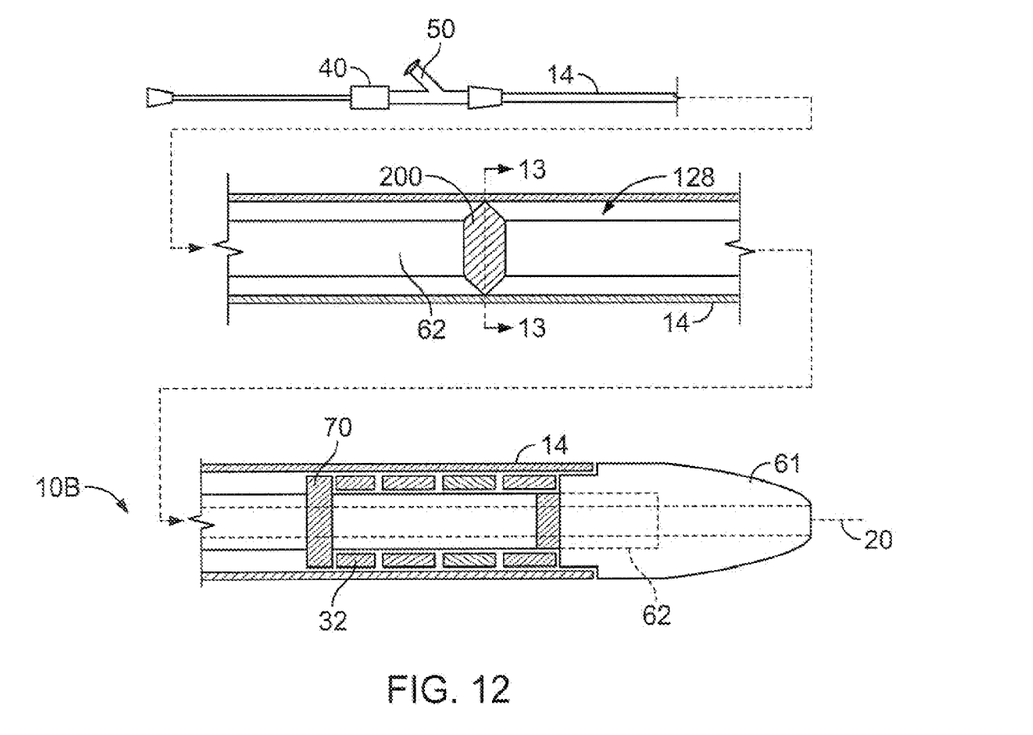
FIG. 12 is an exploded, mixed view of an alternative embodiment of an endoprosthesis delivery system.
Figure 13:
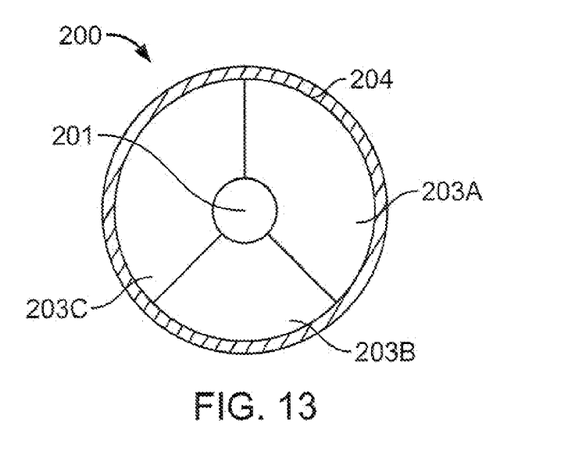
FIG. 13 is a cross-sectional view taken along line 13-13 of FIG. 12, illustrating an embodiment of a spacer.

FIG. 12 shows an implantable medical endoprosthesis system 10B including an inner member 12B. Inner member 12B includes tube 62 and a spacer 200. As shown in FIG. 13, spacer 200 includes an orifice 201 in which tube 62 is disposed. Spacer 200 also includes an outer circumference 204, and orifices 203A, 203B and 203C. With this arrangement, spacer 200 separates at least a portion of outer member 14 from tube 62, while also allowing fluid to flow between outer member 14 and tube 62 via orifices 203A, 203B and 203C. For example, a fluoroscopic dye fluid can flow between tube 62 and outer member 14 to assist in delivering system 10B in a subject and/or to assist in deploying stent 32 at a desired site. Spacer 200 also reduces the surface area of inner member 12B in contact with outer member 14, which can reduce the force used to retract outer member 14 during deployment of stent forces used to retract outer member 14 during deployment of stent 32. This can reduce (e.g., eliminate) compression or buckling of tube 62 as outer member 14 is retracted, which can enhance the accuracy of placement of stent 32 in a desired location.

In general, spacer 200 can be formed of any desired material. Examples of materials from which spacer 200 can be formed include metals, alloys and polymeric materials, such as those noted above. In some embodiments, spacer 200 is formed of a polymer containing nanocomposite particles (e.g., nanoceramic particles). In certain embodiments, spacer 200 includes a coefficient of friction-reducing additive (e.g., a fluoropolymer, a silicone, an ultrahigh molecular weight polyethylene, an oil, or blends thereof) to assist in the movement of outer member 14 with respect to inner member 12B and stent 32. In some embodiments, spacer 200 can have different portions formed of different materials. For example, spacer 200 can include a support material (e.g., a metal, an alloy, a polymeric material) that is partially or entirely coated by a different material (e.g., a relatively low coefficient of friction material, such as a fluoropolymer or a silicone).

In some embodiments, inner member 12B includes a plurality of longitudinally spaced apart spacers 200. In certain embodiments, the distance between nearest neighboring spacers 200 is from about 0.1 inch to about one inch (e.g., from about 0.1 inch to about 0.5 inch). In general, the transverse cross-sectional area of orifices 203A, 203B and 203C is sufficient to provide good fluid flow while separating the inner and outer members. In some embodiments, the transverse cross-sectional area of each of orifices 203A, 203B and 203C is between $3 \times 10^{-6}$ in$^2$ to $1.5 \times 10^{-3}$ in$^2$ (e.g., $9 \times 10^{-6}$ in$^2$, about $1.0 \times 10^{-3}$ in$^2$).

In general, inner member 12B can be prepared as desired. In some embodiments, inner member 12B is prepared as follows. Spacer 200 including orifices 201, 203A, 203B and 203C is made, for example, by machining, injection molding, injection co-molding, casting, or by extrusion or co-extrusion. If extrusion or co-extrusion is used, spacer 200 can be formed by cutting extrudate transversely to a predetermined longitudinal length. Tube 62 is inserted in orifice 201 by, for example, press-fitting tube 62 into the first orifice of the spacer. Alternatively or additionally, tube 62 can be inserted in orifice 201, and then an adhesive can be used to hold tube 62 in place. Examples of adhesives include cyanoacrylate adhesives, including medical grade cyanoacrylate adhesives, such as Loctite® brand products available from Henkel Technologies (e.g., Assure™ 425 Surface Curing Threadlocker).

While certain embodiments have been described, other embodiments are possible.

As an example, while embodiments have been described in which a coil is formed of two different (inner and outer) portions, in certain embodiments a coil may be formed of a single portion, or a coil may be formed of more than two portions (e.g., three layers, four layers, five layers, six layers, seven layers, eight layers, nine layers, 10 layers). In embodiments in which the coil is formed of multiple portions, each portion of the coil may be the same as or different from other portions of the coil.

As an additional example, while embodiments have been described in which there is contact between the inner member and the outer member, in some embodiments the inner member and the outer member are dimensioned so that they are spaced apart. For example, in certain embodiments, the closest distance between the inner member and the outer member may be at least 0.001 inch (e.g., from 0.001 inch to 0.01 inch, 0.005 inch).

As another example, in some embodiments wire 114 is drawn through a resin bath rather than die 120. In certain embodiments (e.g., to toughen the outer portion of the wire), the resin (e.g., a thermoset) can be cured by heat. Optionally, additional materials (e.g., pigments, curing accelerators, fillers, release agents) can be added to the outer portion of wire 100.

As a further example, while embodiments have been described in which a coil has a constant pitch, in certain embodiments, the pitch of the coil can vary, or the coil can include regions in which the pitch varies. For example, a coil can have a first region in which the coil has a constant pitch, and the coil can have a second region in which the coil has a constant pitch that is different from the pitch in the first region of the coil.

As another example, while embodiments have been described in which a coil does not have an end that is adjacent (e.g., contacts) the bumper, in some embodiments one of the ends of the coil is adjacent the bumper.

As an additional example, while embodiments have been described in which an inner member is surrounded by coils or spacers, in some embodiments, an inner member is surrounded by coils and spacers. For example, coils and spacers can alternate along a length of the inner member.

Figure 14:
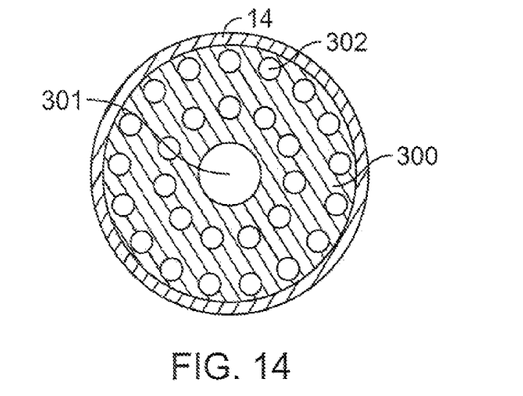
FIG. 14 is a cross-sectional view of an embodiment of a spacer.

As a further example, while a particular design of a spacer has been described, other designs are also possible. In general, in some embodiments, a spacer has an orifice in which the tube is disposed, and at least one additional orifice (e.g., two orifices, three orifices, four orifices, five orifices, six orifices, seven orifices, eight orifices, nine orifices, 10 orifices. For example, FIG. 14 shows a spacer 300 in contact with outer member 14. Spacer 300 includes an orifice 301 (in which the tube can be disposed) and multiple additional orifices 302. In general, the shape of the orifices can be as desired (e.g., circular, square, rectangular, pentagonal, hexagonal, trapezoidal, irregular).

Figure 15:
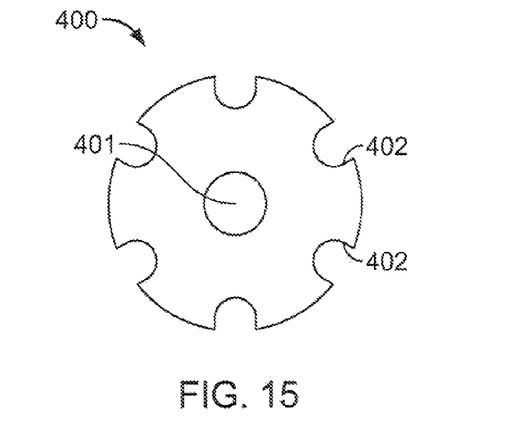
FIG. 15 is a cross-sectional view of a spacer having peripheral cutouts.
Figure 16:
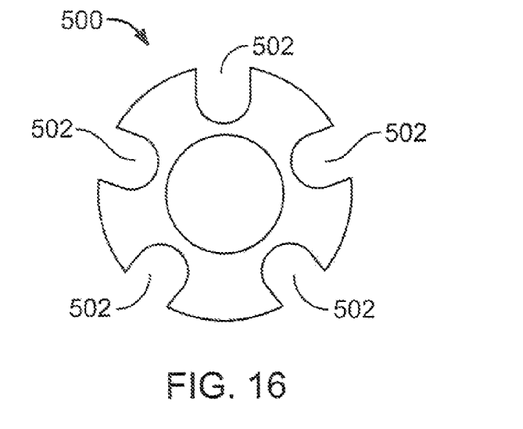
FIG. 16 is a cross-sectional view of a spacer having peripheral cutouts.
Figure 17:
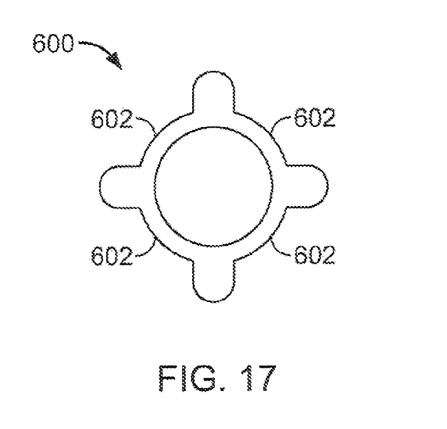
FIG. 17 is a cross-sectional view of a spacer having peripheral cutouts.
Figure 18:
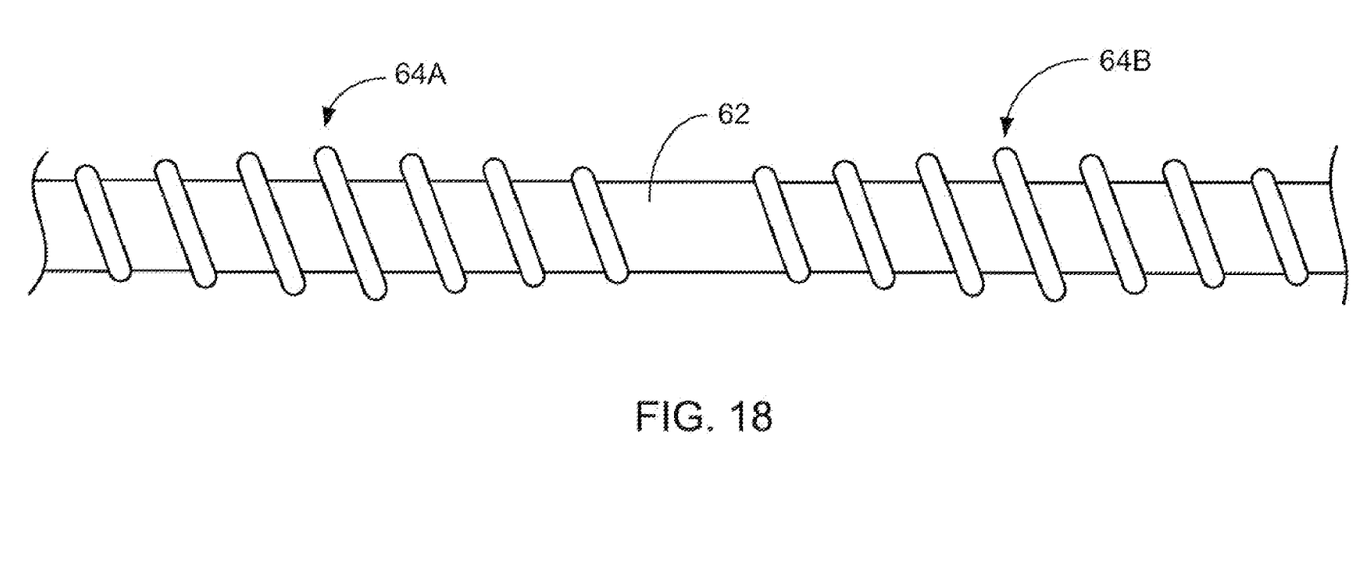
FIG. 18 is a side view of a portion of an inner member of an endoprosthesis delivery system.

As another example, while embodiments have been disclosed in which a spacer includes an orifice in which the tube is disposed and at least one additional orifice, other spacer designs are also possible. For example, FIG. 15 shows a spacer 400 having an orifice 401 and six peripheral cutouts 402. Peripheral cutouts 402 allow for fluid flow between spacer 400 and the outer member. In general, spacer 400 can be formed of any desired material. In some embodiments, spacer 400 is formed of a compressible material (e.g., an elastomer having a Shore A hardness of less than about 80). In certain embodiments, prior to assembly in the system, the maximum transverse dimension of spacer 400 is greater than the minimum transverse dimension of the outer member. For example, prior to assembly in the system, the maximum transverse dimension of spacer 400 can be at least about two percent (e.g., at least about four percent, at least about six percent, between about two percent and about 10%) of the minimum transverse dimension of the outer member. Optionally, spacer 400 can longitudinally taper from a point of contact between spacer 400 and the outer member so that only a portion of a longitudinal length of spacer 400 is in contact with the outer member (e.g., similar to the fashion in which spacer 200 longitudinally tapers). Over-sizing spacer 400 relative to the outer member, and adjusting the amount of longitudinal contact between spacer 400 and the outer member can be advantageously used to adjust the retraction force of the outer member. While FIG. 15 shows a spacer having six peripheral cutouts, a spacer can generally have any number of peripheral cutouts (e.g., one peripheral cutout, two peripheral cutouts, three peripheral cutouts, four peripheral cutouts, five peripheral cutouts, seven peripheral cutouts, eight peripheral cutouts, nine peripheral cutouts, 10 peripheral cutouts). The peripheral cutouts may be evenly distributed or unevenly distributed about the periphery of the spacer. Further, different spacers having the same number of peripheral cutouts can have different designs. For example, FIG. 16 shows a spacer 500 having four peripheral cutouts 502, and FIG. 17 shows a spacer 600 having four peripheral cutouts 602.

In some embodiments in which a spacer longitudinally tapers, at most about 10% (e.g., at most about eight percent, at most about six percent, at most about four percent, at most about two percent) of the longitudinal length of the spacer is in contact with the inner surface of the outer member.

As an additional example, while embodiments have been described in which a self-expanding stent is used, in certain embodiments, the stent can be a balloon-expandable stent. In such embodiments, the inner member typically includes an expandable balloon in the region around which the stent is disposed so that expansion of the balloon results in expansion of the stent.

As another example, while embodiments have been described in which a stent is contained in the system, more generally the systems can contain any implantable medical endoprosthesis. Examples of implantable medical endoprosthesis include stent-grafts and filters (e.g., arterial filters, venus filters).

Other embodiments are in the claims.

What is claimed is:

1. An implantable endoprosthesis delivery system, comprising:
    a tube having an outer surface;
    a coil at least partially surrounding the tube, the coil comprising a first portion having an inner surface, a second portion, and a third portion, the first portion being positioned between the second and third portions, the inner surface of the first portion of the coil being spaced outwardly from the outer surface of the tube and the second and third portions of the coil being in contact with an outer surface of the tube;
    a sheath surrounding and being slidable relative to the tube and the coil, the sheath and the tube being configured so that an implantable endoprosthesis can be disposed between the sheath and the tube;
    an implantable endoprosthesis disposed between the sheath and the tube;
    a bumper disposed on the tube and positioned between the endoprosthesis and the coil;

wherein the sheath surrounds the first portion of the coil; and wherein the first portion of the coil is in contact with the sheath.

2. The implantable endoprosthesis delivery system of claim 1, wherein the implantable endoprosthesis is a self-expanding implantable endoprosthesis.

3. The implantable endoprosthesis delivery system of claim 1, wherein the sheath is axially retractable relative to the tube and the coil.

4. The implantable endoprosthesis delivery system of claim 1, wherein the second and third portions of the coil are attached to the tube.

5. The implantable endoprosthesis delivery system of claim 4, wherein the second and third portions of the coil are integral with the tube.

6. The implantable endoprosthesis delivery system of claim 1, wherein the tube comprises
a proximal end, and
a distal end configured to be inserted into a body lumen, and
wherein the tube defines a first region disposed between the coil and the distal end of the tube, and wherein the implantable medical endoprosthesis is can be disposed around the first region of the tube between the coil and the distal end of the tube.

7. A member, comprising:
a tube comprising
an outer surface,
a proximal end, and
a distal end configured to be inserted into a body lumen;
a coil at least partially surrounding the tube, the coil comprising a first portion having an inner surface, a second portion, and a third portion, the first portion being positioned between the second and third portions,
wherein the inner surface of the first portion of the coil is spaced outwardly from the outer surface of the tube and the second and third portions of the coil are in contact with an outer surface of the tube, and the member is configured for use in an implantable medical endoprosthesis delivery system, and
wherein the tube defines a first region disposed between the coil and the distal end of the tube, the first region being sized so that an implantable medical endoprosthesis can be disposed about the first region of the tube between the coil and the distal end of the tube;
an implantable medical endoprosthesis disposed along the first region;
a bumper disposed on the tube and positioned between the endoprosthesis and the coil;
wherein the member is slidably disposed within a sheath of the implantable endoprosthesis delivery system;
wherein the sheath surrounds the first portion of the coil; and
wherein the first portion of the coil is in contact with the sheath.

8. The member of claim 7, wherein the coil has a first end and a second end opposite the first end, and the first portion of the coil is positioned between the first and second ends of the coil.

9. The member of claim 7, wherein the coil has an end, and one of the second and third portions of the coil is positioned at the end of the coil.

10. The member of claim 7, wherein the member includes a plurality of longitudinally spaced apart coils, at least some of the coils having first, second, and third portions.

11. The member of claim 10, wherein a longitudinal spacing between each coil and its nearest neighboring coil is from about 0.1 inch to about one inch.

12. The member of claim 7, wherein windings of the coil have a longitudinal pitch of from 0.005 inch to about 0.1 inch.

13. The member of claim 7, wherein a spacing between the outer surface of the tube and the inner surface of the first portion of the coil is from 0.005 inch to about 0.1 inch.

14. The member of claim 7, wherein the coil includes an inner portion and an outer portion that surrounds the inner portion.

15. The member of claim 14, wherein the inner portion of the coil comprises a metal or an alloy.

16. The member of claim 14, wherein the outer portion of the coil comprises a polymer.

17. The member of claim 16, wherein the polymer comprises a thermoplastic or a thermoset.

18. The member of claim 16, wherein the polymer comprises a fluoropolymer.

19. The member of claim 7, wherein the second portion comprises a first end of the coil and the third portion comprises a second end of the coil opposite the first end.

20. The member of claim 7, wherein the second and third portions of the coil are attached to the tube.

21. The member of claim 20, wherein the second and third portions of the coil are integral with the tube.

22. The member of claim 7, wherein the implantable endoprosthesis is a self-expanding implantable endoprosthesis.

* * * * *